US006592368B1

(12) United States Patent
Weathers, Jr.

(10) Patent No.: US 6,592,368 B1
(45) Date of Patent: Jul. 15, 2003

(54) DENTAL CORTICAL PLATE ALIGNMENT PLATFORM

(76) Inventor: Arthur K. Weathers, Jr., 14 Hudson Rd., Griffin, GA (US) 30224

( * ) Notice: Subject to any disclaimer, the term of this patent is extended or adjusted under 35 U.S.C. 154(b) by 0 days.

(21) Appl. No.: 09/561,888

(22) Filed: May 1, 2000

(51) Int. Cl.[7] ............................. A61C 3/02; A61B 17/17
(52) U.S. Cl. ........................................... 433/76; 606/96
(58) Field of Search .............................. 433/74, 75, 76, 433/215, 165, 134; 606/80, 97, 98

(56) References Cited

U.S. PATENT DOCUMENTS

| | | | | |
|---|---|---|---|---|
| 2,181,746 A | * | 11/1939 | Siebrandt | 606/98 |
| 2,531,734 A | * | 11/1950 | Hopkins | 606/97 |
| 3,508,334 A | * | 4/1970 | Weissman | 433/76 |
| 5,173,050 A | * | 12/1992 | Dillon | 433/165 |
| 5,403,322 A | * | 4/1995 | Herzenberg et al. | 606/98 |
| 5,484,285 A | * | 1/1996 | Morgan et al. | 433/76 |

* cited by examiner

Primary Examiner—Todd E. Manahan

(57) ABSTRACT

This application relates to a dental apparatus for the initial and subsequent guidance of drills, hypodermic needles, or drug delivery devices into the cortical plate of human mandibular and maxillary bones. The invention comprises a thin platform with one or a plurality of angled or straight preformed perforations serving as entrance ports. Each port is optimally heralded by a radio-opaque marker to enable a view of the tooth root prior to drilling for a superior selection of a nerve deadening site and a whisker tubule visually displaying the drill's angle. The platform can be positioned on either the inner or outer side of the cortical plate, and is optimized for use with a dedicated indexing bite apparatus, a dedicated rubber dam style clamp, or by attachment to a RINN positioner or the like.

19 Claims, 2 Drawing Sheets

DENTAL CORTICAL PLATE ALIGNMENT PLATFORM

This application relates to the field of medicine, and more specifically involves corrective measures to improve the success of intraosseous medication injections in Dentistry and related fields requiring anaesthesia.

DISCUSSION OF THE PRIOR ART

The art of deadening pain for the Dental industry was greatly improved by the discovery that smaller and more effective dosages of medication could be introduced beneath the cortical plate. Pivotally, U.S. Pat. No. 5,173,050 by Dillon in 1992 cited methods of and implements for drilling an initial perforation, thus allowing the dentist to remove the drill and re-enter the passageway with a hypodermic needle to deliver anaesthesia.

However, difficulties as taught by Dillon mainly involving failures of re-entry caused the industry to respond with two U.S. Pat. No 5,762,639 by Gibbs, and U.S. Pat. No. 5,779,708 by Wu, both describing methods to leave an intraosseous channel in place subsequent to drilling. This channel served as a guidance system to allow re-entry for medicative purposes.

Adversely, the necessity of hollow guidance sleeves to themselves be drills increased the expense over Dillon and introduced dangers involving incidents of breakage of the tiny-diameter, hollow implements. The threat of the breakage and subsequent successful retrieval of all foreign objects from the patient is complicated by the presence as taught by Gibbs and Wu of other separate and intricate inner plugging stylets or rods. These latter implements strengthen the overall shaft and block the backflow of bone chips and other organic matter while drilling. Also the health of the patient is subsequently put at risk by the open channel, which in some cases puts bacteria in open contact with the tissues beneath the bone for several hours.

Thus the introduction of bacteria from the air or contaminated water lines, the post recovery after inevitable failure of some instruments, and the more complicated nature of drill construction has dampened the success of the latter two patents. Because of the simplicity of the concept and the fact the Dillon apparatus allows the flesh around the perforation to seal the wound when no drill or needle is present, the commercial success and availability of this patent has flourished under the marketing name of the Stabident system. But the original complaint of difficult re-enty (for the Stabident system and other related prior art teaching such as the Villette injector) remains as a drawback for optimized delivery of medication.

Another pertinent negative to all three patents mentioned is the fact breakage of the drill or apparatus is prone to happen flush to the cortical plate. This is because the drill is hand held and success is dependent on the ability of the Dentist to maintain the angle of entry while penetrating the hard surface to reach the interior cancellous bone tissue. The patient may waver, the Dentist may move improperly, or the fabricating material may fail. The ability to retrieve the broken material is thus a serious issue.

OBJECTS AND ADVANTAGES

It is therefore accordingly an object of the present invention to provide a guidance channel exterior to the cortical plate heralded by radio-opaque markers to enable the checking of the positioning of the contemplated penetration at the time of X-rays, lessening the danger of having to drill a second entry, and/or inflicting damage to an unsuspected curved root.

It is further accordingly an object of the present invention to provide a guidance channel exterior to the cortical plate while simultaneously providing a precise anchoring device for X-ray film or devices, especially those of digital imagery where the sensor is thicker than the older models.

It is further accordingly an object of the present invention to provide a guidance channel exterior to the cortical plate to enable the angle of entry through the bone to be maintained as the penetrating drill passes through the bone, lessening the danger of breakage.

It is further accordingly an object of the present invention to provide a guidance channel exterior to the cortical plate to enable successful re-entry of the orifice by aligning the medicating needle tip back to the correct location, lessening trauma to the gingiva.

It is further accordingly an object of the present invention to provide a guidance channel exterior to the cortical plate to enable the angle of entry through the bone to be maintained as the medicating needle is subsequently inserted through the bone, lessening the danger of breakage.

It is further accordingly an object of the present invention to provide a guidance channel exterior to the cortical plate to provide a short protruding stem to grasp and remove should breakage of the drill, needle, or delivery device occur, lessening the danger of drills, needles, or delivery devices being broken flush to the cortical plate and slightly beneath the gingiva.

It is further accordingly an object of the present invention to provide a guidance channel exterior to the cortical plate to provide a precise predetermined angle of entry such as 29 degrees to the perpendicular, increasing success in the rear molar regions.

It is further accordingly an object of the present invention to provide a guidance channel exterior to the cortical plate while providing a visual aid herein termed a whisker to assist the dentist in maintaining a precise predetermined angle of entry such as 29 degrees to the perpendicular, decreasing incidents of breakage in the rear molar regions.

It is further accordingly an object of the present invention to provide a guidance channel exterior to the cortical plate that does not maintain a channel for airborne or waterborne bacteria to enter the underlying tissues.

These and many other objects and advantages will be readily apparent to one skilled in the art to which the invention pertains from a perusal of the claims and the following detailed description of preferred embodiments when read in conjunction with the appended drawings.

BACKGROUND OF THE INVENTION

The placement of a guidance platform exterior to, but flush against, the cortical plate allows a selection of preformed entry points. These entry points are optimally near a small amount of semi (or fully) radio-opaque material. A Dentist can then position the platform at the best assumed position, and perform an X-ray of the subject tooth as usual, but have the alignment holes appear on the X-ray film as small circles or markers and confirm the position. Otherwise as is sometimes the case in intraosseous drilling, a crowded, curved, or deformed root may be struck with subsequent unwarranted damage to the ligaments or to the tooth itself, exposing it to infection. The drilling port chosen after the X-ray can be highlighted by the presence of color coding introduced by the Dentist on the surface of the guidance platform by a magic marker type implement.

The contact side of the platform may be slightly beveled to reflect the natural curvature of the gingiva covering the cortical plate.

The multiple holes of the guidance platform can be angled with some at right angles and some slanted. A typical slanted example for molars would be 29 degrees up from the perpendicular, which is the same as 61 degrees from the plane of the surface of the cortical plate. Although frontal teeth may be reached with ease, the rear teeth usually require the Dentist to come at the bone off the perpendicular due to the inner cheeks of the patient. Also, in actual practice the correct placement of the drill between the molars diminishes the more to the rear the desired location is.

A short tubule of soft plastic termed a whisker is contemplated to rise from the guidance platform at the angle of the guidance port. This gives a Dentist a visual reference to initially and subsequently hold the drilling apparatus at the correct angle to match the desired angle known to produce the best results. Thus the whisker tubule takes the guess work out of holding a drill or needle at the best angle relative to the cortical plate.

The guidance platform itself may be attached to prior art apparatus such as a RINN positioner, rubber dam, or X-ray bite blocks if subsequent re-entry to the hole is not required after the initial injection of medication. However, a dedicated method of attachment to a customized bite-block or two-component polycarbon such as polyvinyl, through a vertically adjustable connector would be better. The subsequent ability of an indexed system to accurately reposition the guidance platform eliminates the probing and searching associated with the Stabident and other nonguided systems when the pain is returning and the patient needs more nerve deadening. This is true especially in the extremely posterior positions on the lingual (or tongue) side where the Dentist may have to otherwise search for the tiny hole with a mirror.

The ability of the indexed guidance platform to be accurately reinserted into the mouth eliminates the problem, and once again allows immediate access. The indexing may be achieved by having the patient bite down on a wedge of impressionable material such as medical grade Styrofoam tailored to that purpose. Alternately, fast hardening two-component impression material such as medical grade polyvinyls may be placed while viscous over both a tooth and plastic inserts termed strap runners. These polyvinyls are available in clear uncolored varieties and are designed to receive the bite and create the indexed surface within a forty second set time. Since the strap runners are a suitable containment medium and are embedded in the polyvinyl, this system can be used in lieu of a bite block and is the preferred embodiment due to the superior indexing. With either system, bite block or polyvinyl, the inner lingual side can connect to a clothes-pin type connector or the like to fasten an X-ray film along the inside of the subject tooth.

As a third style of embodiment more useful for root canal procedures, a clamped anchoring system that fastens to the base of the tooth is contemplated to be left in place in the mouth for the duration of the visit, with the guidance platform left in place underneath a rubber dam which can be peeled back at will. Alternately in cases where its presence may impede the Dentist, the guidance platform may be snapped out from its locking mechanism or flipped out of position in such a manner that it can be returned to service as required.

These dedicated embodiments also allow a better accommodation to the much thicker sensor plate of digital imagery X-rays. Current methods of alignment are not typically done with an indexed system, which often defeats the precise placement the expensive digital imagery requires.

The guidance platform is connected to the anchoring system by a precise clamp for systems using prior art devices such as a RINN positioner, or in dedicated systems by a molded plastic arm that before installation curls the platform inward. By pulling the platform outward by hand or with small clamps and having the patient bite down on the indexing block, the platform can then be released to be carried snugly inward against the gingiva by the gentle force of the plastic arm returning to its natural curvature.

Also the up or down height of the platform can be adjusted by the use of a trombone lock or the like, which allows the Dentist to choose and then set in place the optimum vertical location of the drilling port relative to the jawbone. This adjustment covers the variance between adult or children, and is regulated by pulling back the wedge of the trombone lock out of its notch, sliding the plastic arm up or down, and releasing the wedge back into another underlying notch.

The physical presence of the guidance platform directly against the gingiva in almost all cases ensures that if a break of the drill or needle occurs, after removal of the guidance platform there will be an elevated stub protruding that is easily grasped and retrieved. This is a tremendous assist to the Dentist and avoids possible trauma and/or surgery to the patient to remove buried implements in or beyond the cortical plate.

DETAIL DESCRIPTION OF PREFERRED EMBODIMENT

Figure 1:
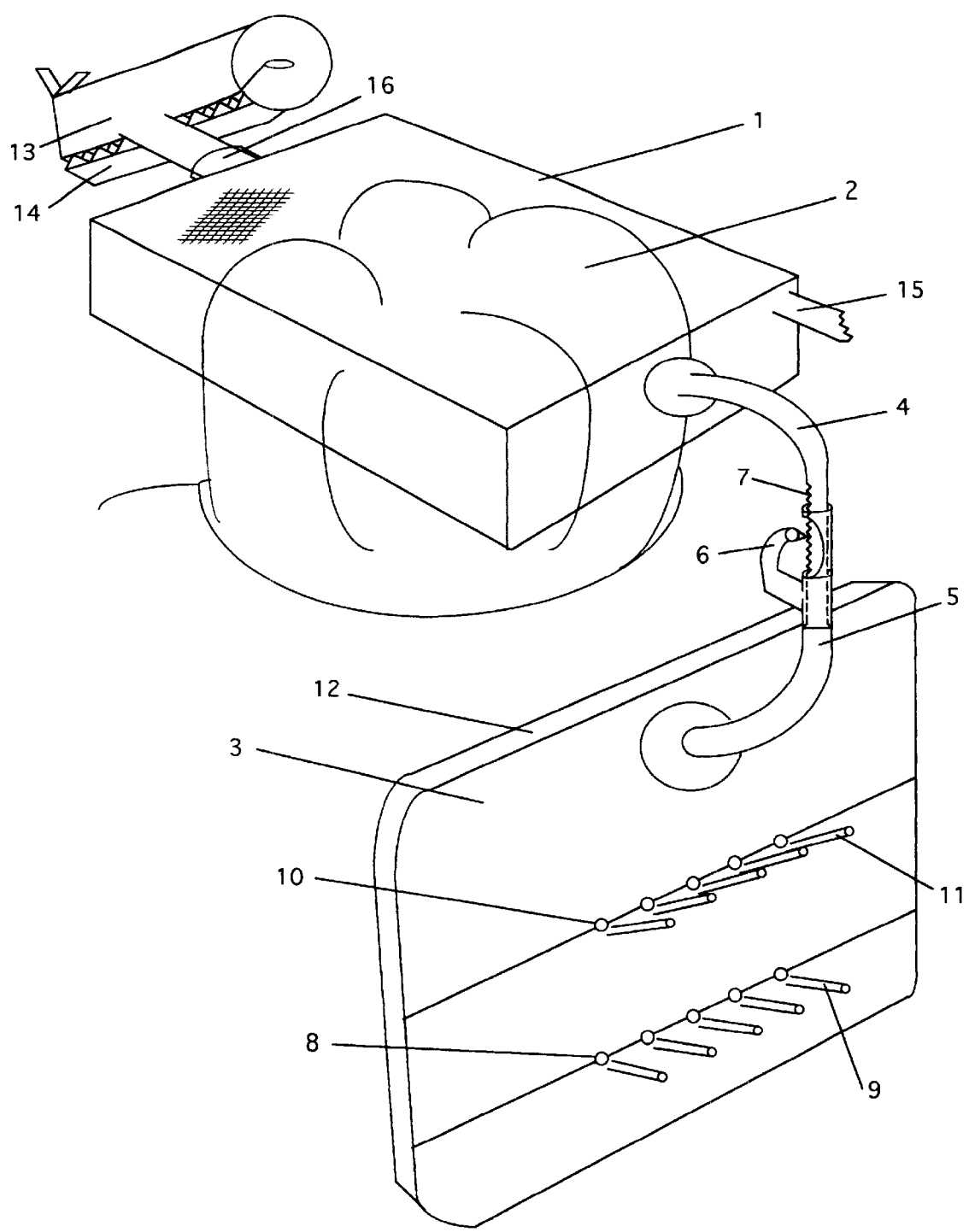
FIG. 1 is a drawing detailing an embodiment of the invention using a bite block as the anchoring means to the tooth.

FIG. 1 bite block 1 is shown in transparent outline form over a lower left molar 2 of a patient. As seen by the crosshatching, the upper surface is solid. To connect block 1 to guidance platform 3, arcing down from the facial (cheek) side is adjustment arm 4, which is positioned inside the uplifted arm 5 rising from the guidance platform itself. The flexible wedge 6 together with the serrated edge 7 of upper arm 4 creates a trombone lock which can be elevated by the Dentist about three millimeters or lowered as much as five millimeters from the initial position. In both drawings the female element 5 bearing the wedge 6 is shown attached to the platform 3, but this is one aspect of a reversible arrangement whereby the serrated male element 7 could have been at the terminal end of the arm connected to the platform with arm 5 connected to the bite block.

A line of horizontal drilling ports 8 are positioned about ten to twelve millimeters below the crown of molar 2, which automatically positions them adjacent a choice site of the cortical plate for deadening purposes. Each port is sized just large enough to allow a drill or needle clear entry (examples would be either 25 or 27 gauge), and the ports are about one millimeter apart. Added in the manufacturing process is a short complementary whisker 9 of soft nylon or the like to give a visual drilling path for the dentist to align the drill through the guidance platform 3, which is itself made of a dense, hard plastic. Whisker 9 stands out from port 8 at ninety degrees, which is an angle of entry usually used with front teeth.

A line of horizontal drilling ports 10 all having a whisker 11 angled sixty one degrees (or twenty nine degrees from vertical) are also placed in a horizontal line about three millimeters above port 8. The thickness of guidance platform 3 is about three millimeters as seen along edge 12.

The upper jaw 13 and the lower jaw 14 of a typical X-ray plate clamping system are provided to fasten an X-ray film (not shown) to the lingual (inner) side of tooth 2. Connector 15 goes out the mouth to a guide funnel (not shown) to channel the X-rays for validation of the prospective drilling sites. Telescoping tube 16 allows the X-ray clamp to be adjusted in or out.

All of the whiskers such as 9 or 11 have a semi or full radio-opaque disk at the base (not shown) which is displayed to the Dentist in the X-ray as a string of dark shadows or black specks. Also a vertical series of similar tiny markers (not shown) can ascend along the lateral outer edge of the guidance platform synchronized with the notches of serrated edge 7. This provides a means of indicating the number of notches up or down the Dentist may wish to alter the vertical alignment of the guidance platform itself.

Bite block 1 is indexed to the shape of the upper and lower teeth when the patient bites down, which allows the entire block and connections to first be removed, and then returned later in such a way the ports resume their former location. The sixty one degree angle of port 10 is preserved even when the bite block is used for the upper teeth (not shown).

Figure 2:
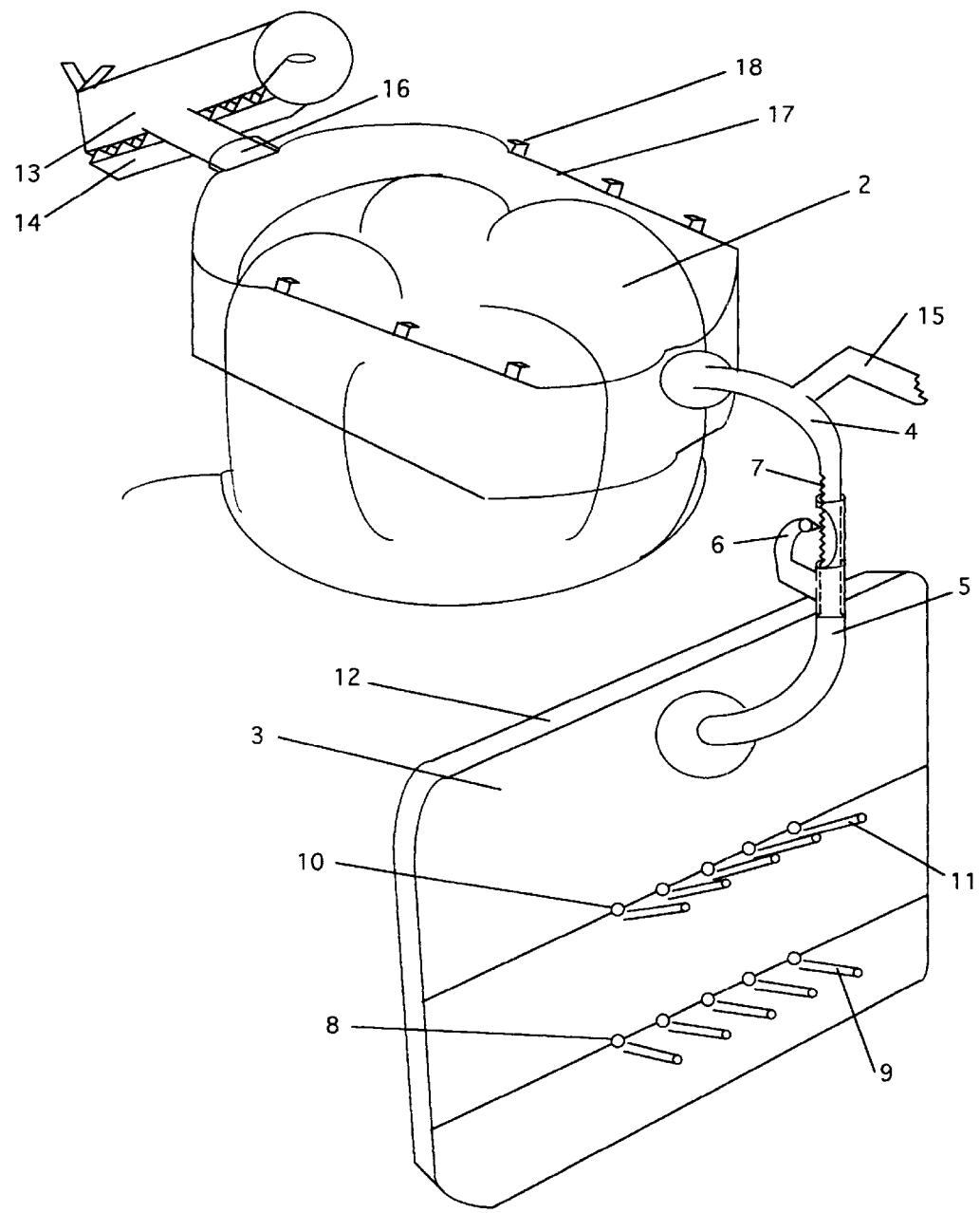
FIG. 2 is a drawing detailing the preferred embodiment of the invention using strap runners as the anchoring means to the tooth.

In FIG. 2, an alternate and more precise indexing system would be obtained with a typical two component polycarbon (not shown) such as the various polyvinyls that set up hard in under forty seconds. This allows the Dentist sufficient time to position the guidance platform and other peripherals such as an X-ray clamp if deemed necessary. The rubber solidifies around connector arms termed strap runners 17, thus creating an entire apparatus specific to the patient. Protrusion 18 gives the polyvinyl improved adherence to the strap runners 17, which can come in various sizes to accommodate all types of teeth. Polyvinyl before curing has the consistency of silly putty and does not drip, so connected platforms also work for upper teeth. Funnel connector 15 arises from arm 4 as a variation.

Rather than a bite block as shown, a prior art fastener such as is used in rubber dams (not shown) can be substituted as the central anchoring system. These types of fasteners are in general not as accurate when repositioned as either of the indexed systems described above, but have the advantage that once in place are not generally removed until after the need for more anaesthesia has passed. Thus the port and the cortical bone entry hole remain synchronized for further dispensing of medication.

It should be noted that if a Dentist was willing to give up the advantages of an adjustable intermediary such as the trombone lock illustrated, the upper edge of the guidance platform could for example be given small protuberances to allow it to be pressed against polyvinyl directly. Especially if enough holes are present in the guidance platform to offer multiple choices, this would allow a direct connection to the polyvinyl (or a bite block or rubber dam clamp if they were engineered this way). The usefulness of the X-ray validation of a drilling site has been described, but the invention should not be seen as dependent on this benefit. Although presented as an aid in Dental procedures, the invention can find use in other medical fields employing perforations of bone for humans or other species.

This invention should not be confined to the embodiments described, as many modifications are possible to one skilled in the art. This paper is intended to cover any variations, uses, or adaptations of the invention following the general principles as described and including such departures that come within common practice for this art and fall within the bounds of the claims appended herein.

I claim:

1. A guidance device for facilitating the controlled perforation of the cortical area of the jawbone of humans or other species for subsequent injection of fluids, comprising a thin plate penetrated by a minimum of one straight passage, said thin plate made of a hard plastic or other durable composite or pure material sufficiently dense to channel the route of a dental drill through said passage without structural failure of purpose, said straight passage following a fixed line, said fixed line creating an angle between forty-five and ninety degrees to the general plane containing the majority of said thin plate;

where said thin plate has a connecting extension emanating from one face near to or on the border of said thin plate, said extension of sufficient length to serve as a means of attachment to further dental apparatus;

together with the second half of an adjustable trombone lock, such that the far end of said extension is of a shape to serve as one or the other component of said trombone lock, such that said second half is complementary to connect with said extension, and such that the distant end of said second half terminates in a bite block, or terminates in a strap runner suitable to be adhered to vulcanizing rubber dam, or terminates in an attachment means suitable to interface with said bite block, said strap runner, or said clamping device.

2. A guidance device as in 1, where the farthest end of said bite block, or said strap runner, or said clamping device has means suitable for the connection of an X-ray film or sensor, such that said thin plate approximately lies in a plane parallel to another plane containing said X-ray film or sensor, and with such distance of separation that a subject tooth may be present between said thin plate and said X-ray film or sensor.

3. A guidance device as in 1, where said adjustable trombone lock is replaced by non-adjustable locking means.

4. A guidance device for facilitating the controlled perforation of the cortical area of the jawbone of humans or other species for subsequent injection of fluids, comprising a thin plate penetrated by a minimum of one straight passage, said thin plate made of a hard plastic or other durable composite or pure material sufficiently dense to channel the route of a dental drill through said passage without structural failure of purpose, said straight passage following a fixed line, said fixed line creating an angle between forty-five and ninety degrees to the general plane containing the majority of said thin plate;

where said thin plate has a connecting extension emanating from one face near to or on the border of said thin plate, said extension of sufficient length to serve as a means of attachment to further dental apparatus;

where said extension is of a narrowness and length such that said extension may be flexed by a Dentist, and subsequently upon release said extension will seek to return to its unflexed shape.

5. A guidance device for facilitating the controlled perforation of the cortical area of the jawbone of humans or other species for subsequent injection of fluids, comprising a thin plate penetrated by a minimum of one straight passage, said thin plate made of a hard plastic or other durable composite or pure material sufficiently dense to channel the route of a dental drill through said passage without structural failure of purpose, said straight passage following a fixed line, said fixed line creating an angle between forty-five and ninety degrees to the general plane containing the majority of said thin plate;

together with either a semi radio-opaque or fully radio-opaque material, where one or the other opening port of said straight passage is located in close approximation to said radio-opaque material, whereas said material is of a size roughly similar to the size of said opening port.

6. A guidance device for facilitating the controlled perforation of the cortical area of the jawbone of humans or other species for subsequent injection of fluids, comprising a thin plate penetrated by a minimum of one straight passage, said thin plate made of a hard plastic or other durable composite or pure material sufficiently dense to channel the route of a dental drill through said passage without structural failure of purpose, said straight passage following a fixed line, said fixed line creating an angle between forty-five and ninety degrees to the general plane containing the majority of said thin plate;

together with a narrow whisker attached to a surface of said thin plate, said whisker of a composition firm enough to hold itself straight under the force of gravity, but pliable enough to yield back from tactile pressure, said whisker located on said thin plate in close approximation to one or the other opening port of said straight passage, whereas the established angle said whisker forms with said thin plate is approximately parallel with said angle of said straight passage.

7. A guidance device as in 5, or 6, where a portion of the border of said thin plate is shaped sufficient, or textured sufficient, or engineered with anchoring protuberances sufficient to allow adhesion to a small mass of vulcanizing rubber.

8. A guidance device as in 4, 1, 5, or 6, where said thin plate is penetrated by a plurality of said straight passage, said plurality of passages of like configuration and like angle relative to said general plane;

where said plurality of passages are arranged such that a straight, line traveling along one side of said thin plate will pass through the entry port located on said side of each of said plurality of passages;

where the distance between any adjacent two of said plurality of passages is approximately one millimeter, within a tolerance of three fourths of a millimeter.

9. A guidance device as in 4, 1, 5, or 6, where said angle is ninety degrees approximately, but no less than eighty degrees.

10. A guidance device as in 4, 1, 5, or 6, where said angle is sixty one degrees approximately, within a tolerance of less than nineteen degrees.

11. A method of administering medication through cortical bone, said method comprising the steps of:

securing a guidance platform in close conjunction with the gingiva over said cortical bone, said guidance platform containing a straight channel crafted to a desired angle of entry, said channel of a size to accommodate and pass the drill bit of a handheld dental drilling apparatus;

drilling an opening in said cortical bone with said drill bit through said guidance platform;

withdrawing said drill bit and injecting medication into said channel and said opening respectively with a hollow drug delivery device an example of which is a hypodermic needle;

withdrawing said drug delivery device and allowing said medication to produce an effect on the patient.

12. A method of administering medication as in 11, wherein the step of securing said guidance platform is accomplished by connective means from said guidance platform to a RINN positioner serving as an anchoring means.

13. A method of administering medication as in 11, wherein the step of securing said guidance platform is accomplished by connective means from said guidance platform to a rubber dam serving as an anchoring means.

14. A method of administering medication as in 11, wherein the step of securing said guidance platform is accomplished by connective means from said guidance platform to a bite block serving as an anchoring means.

15. A method of administering medication as in 11, wherein the step of securing said guidance platform is accomplished by connective means from said guidance platform to vulcanizing rubber serving as an anchoring means.

16. A method of administering medication as in 12, 13, 14, or 15, wherein the additional step of obtaining an X-ray is further performed;

whereby an X-ray film or sensor is part of the connection to said guidance platform on the far side of said anchoring means in such a manner that a subject tooth would be between said guidance platform and said anchoring means, and where said channel is accompanied in close proximity by a small portion of semi or fully radio-opaque material sufficient to appear on said X-ray.

17. A method of administering medication as in 16, wherein after said step of obtaining said X-ray the additional step of elevating or lowering said guidance platform is performed by altering the position of an adjustable lock utilized as said connective means from said guidance platform to said anchoring device;

wherein said guidance platform has a plurality of similar channels, with each of said channels accompanied by a similar small portion of said radio-opaque material;

wherein the additional step of choosing one of said plurality of channels is performed after obtaining said X-ray.

18. A method of administering medication as in 11, wherein the additional step of aligning said drill bit to follow or match the indicated angle of a whisker is performed before said step of drilling said opening in said cortical bone, wherein said whisker is attached to a surface of said guidance platform, said whisker of a composition firm enough to hold itself straight under the force of gravity, but pliable enough to yield back from tactile pressure, said whisker located on said guidance platform in close approximation to one or the other opening port of said straight passage, whereas the established angle said whisker forms with said guidance platform is approximately parallel with said angle of said straight passage.

19. A method of administering medication as in 11, wherein the additional step of removing said guidance platform from said gingiva is performed;

further the additional step is performed of again securing said platform in close conjunction with said gingiva when said medication is weakening;

further the additional step is performed of again injecting additional medication into said channel and said opening respectively with the same or another hollow drug delivery device;

and further the additional step is performed of again withdrawing said drug delivery device and again removing said guidance platform from said close conjunction with said gingiva.

* * * * *